United States Patent
Pham Duc et al.

(10) Patent No.: US 9,969,662 B2
(45) Date of Patent: May 15, 2018

(54) METHOD FOR SEPARATING OLEFINS WITH GENTLE CLEAVAGE

(71) Applicant: LINDE AKTIENGESELLSCHAFT, Munich (DE)

(72) Inventors: Tuat Pham Duc, Penzberg (DE); Holger Schmigalle, Geretsried (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 552 days.

(21) Appl. No.: 14/390,922

(22) PCT Filed: Apr. 2, 2013

(86) PCT No.: PCT/EP2013/000973
§ 371 (c)(1),
(2) Date: Oct. 6, 2014

(87) PCT Pub. No.: WO2013/149721
PCT Pub. Date: Oct. 10, 2013

(65) Prior Publication Data
US 2015/0065770 A1 Mar. 5, 2015

(30) Foreign Application Priority Data
Apr. 5, 2012 (DE) .................. 10 2012 006 992

(51) Int. Cl.
C07C 7/11 (2006.01)
C07C 4/04 (2006.01)
(Continued)

(52) U.S. Cl.
CPC ................ C07C 7/11 (2013.01); B01J 19/24 (2013.01); C07C 4/04 (2013.01); C10G 9/00 (2013.01);
(Continued)

(58) Field of Classification Search
CPC .... C07C 7/11; C07C 4/04; C10G 9/00; C10G 9/02; Y02P 30/464; B01D 2252/20;
(Continued)

(56) References Cited

U.S. PATENT DOCUMENTS 2,014,724 A * 9/1935 Eastman ................. C07C 5/327
585/648
2,464,810 A * 3/1949 Hirsch ................... C10G 11/18
208/113
(Continued)

FOREIGN PATENT DOCUMENTS

DE 10 2006 045498 A1 4/2008
EP 1158038 A2 11/2001
(Continued)

OTHER PUBLICATIONS

International Search Report for PCT/EP2013/000973 dated Aug. 23, 2013.
(Continued)

*Primary Examiner* — Philip Louie
*Assistant Examiner* — Aaron Pierpont
(74) *Attorney, Agent, or Firm* — Millen White Zelano & Branigan, PC

(57) ABSTRACT

In a process for producing olefins, a hydrocarbon-containing feed is fed into a cracking furnace where relatively long-chain hydrocarbons of the hydrocarbon-containing feed are cracked at least partly to form shorter-chain olefins, encompassing ethylene and propylene. Cracking gas (1) formed during cracking is conveyed in succession through an upper section (11) and a lower section (12) of a scrubbing column (10) in countercurrent to a liquid scrubbing medium (43, 31), is proposed. A fraction (43) rich in petroleum spirit is used in the lower section (11) of the scrubbing column (10) and a water-rich fraction (31) is used in the upper section
(Continued)

(11) of the scrubbing column (10) as scrubbing medium (43, 31). A plant configured for carrying out the process is likewise provided by the present invention.

15 Claims, 3 Drawing Sheets

(51) Int. Cl.
*B01J 19/24* (2006.01)
*C07C 7/00* (2006.01)
*C10G 9/00* (2006.01)
*C10G 9/36* (2006.01)

(52) U.S. Cl.
CPC .............. *C10G 9/36* (2013.01); *B01J 2219/24* (2013.01); *C10G 2400/20* (2013.01); *Y02P 30/464* (2015.11)

(58) Field of Classification Search
CPC .............. B01D 2252/205; B01D 53/14; B01D 53/1406; B01D 53/1487; B01D 53/1493; B01D 53/18; B01D 53/185
USPC .......................... 585/324, 648; 422/611, 612
See application file for complete search history.

(56) References Cited

U.S. PATENT DOCUMENTS

| 3,060,116 | A | * | 10/1962 | Hardin, Jr. ................ C10L 1/06 208/79 |
| 3,691,058 | A | * | 9/1972 | Hammer ................ C10G 47/00 208/104 |
| 3,923,921 | A | | 12/1975 | Kohfeldt et al. |
| 4,041,129 | A | * | 8/1977 | Foster ................ B01D 53/1418 205/496 |
| 4,060,399 | A | * | 11/1977 | Gleason ............... B01D 47/025 261/114.1 |
| 4,548,706 | A | * | 10/1985 | Papadopoulos .......... C10G 9/00 208/130 |
| 4,831,205 | A | * | 5/1989 | Krambeck ............... C07C 11/02 585/519 |
| 5,464,536 | A | * | 11/1995 | Rogers ............... B01D 17/0217 210/360.1 |
| 6,013,852 | A | * | 1/2000 | Chandrasekharan .. C10G 55/04 208/88 |
| 6,235,961 | B1 | | 5/2001 | Kurukchi et al. |
| 7,011,740 | B2 | | 3/2006 | Tallman et al. |
| 2001/0042700 | A1 | * | 11/2001 | Swan, III ............... C10G 69/04 208/68 |
| 2004/0069684 | A1 | | 4/2004 | Tallman et al. |
| 2005/0150817 | A1 | * | 7/2005 | Tallman ................ C10G 51/06 208/78 |
| 2007/0265482 | A1 | * | 11/2007 | Tsunoda .................... C07C 4/06 585/651 |
| 2008/0146857 | A1 | * | 6/2008 | Verma .................... B01D 3/143 165/60 |
| 2010/0147780 | A1 | * | 6/2010 | Endo .................... G01N 1/4077 210/768 |
| 2011/0041685 | A1 | * | 2/2011 | Tanaka ............... B01D 53/1412 95/16 |

FOREIGN PATENT DOCUMENTS

| EP | 1413621 A1 | 4/2004 | |
| GB | 851437 A | * 10/1960 | ............. C07C 7/005 |
| WO | 9312200 A1 | 6/1993 | |
| WO | WO 9312200 A1 | * 6/1993 | ............. C10G 9/002 |
| WO | 0044694 A1 | 8/2000 | |

OTHER PUBLICATIONS

English Abstract of DE102006045498, Publication Date: Apr. 10, 2008.

English Abstract of EP1158038, Publication Date: Nov. 28, 2001.

* cited by examiner

Prior Art

METHOD FOR SEPARATING OLEFINS WITH GENTLE CLEAVAGE

The invention relates to a process and an apparatus for producing olefins, in which a liquid hydrocarbon-containing feed is fed into a cracking furnace where relatively long-chain hydrocarbons of the hydrocarbon-containing feed are cracked to form shorter-chain olefins, including ethylene and propylene.

In such a process, the hydrocarbon-containing feed is fed together with steam into a cracking furnace of an appropriate apparatus and heated there by means of thermal radiation to such an extent that the relatively long-chain hydrocarbons of the hydrocarbon-containing feed are cracked to give the shorter-chain olefins. The liquid hydrocarbon-containing feed which is used in the context of the present application consists predominantly of saturated relatively long-chain hydrocarbons. In this case, the hydrocarbon-containing feed has a boiling point of from about −40° C. to 600° C. Such feeds are, for example, known in the prior art as naphtha, atmospheric gas oil, kerosene, hydrogenated or unhydrogenated heavy/high-boiling hydrocarbon mixtures. Liquid C3/C4 fractions (liquefied petroleum gas) can likewise serve as feed for cracking for the purposes of the invention.

For the purposes of the present invention, a "cracking furnace" is a cracking unit in which the cracking conditions are established. It is possible for a total furnace to be divided into two or more cracking furnaces. These are then frequently referred to as furnace cells. A plurality of furnace cells belonging to a total furnace generally have independent radiation zones and a joint convection zone and also a joint fume extraction. In these cases, each furnace cell can be operated with its own cracking conditions (see below). Each furnace cell is thus a cracking unit and is consequently referred to here as a cracking furnace. The total furnace then has a plurality of cracking units or, in other words, a plurality of cracking furnaces. If only one furnace cell is present, this is the cracking unit and thus the cracking furnace. Cracking furnaces can be assembled to form groups which are, for example, supplied with the same feed. The cracking conditions within a furnace group are generally set so as to be identical or similar. The invention can be carried out using one or more cracking furnaces.

Cracking of the hydrocarbon-containing feed forms a mixture which is gaseous at the temperatures at the outlet of the cracking furnace(s) and contains the olefins to be isolated, in particular ethylene and propylene. The gaseous mixture formed during cracking is referred to as cracking gas. The cracking gas leaving the cracking furnace subsequently has to be freed of impurities by means of a series of purification steps and separated into the individual hydrocarbon fractions, in particular ethylene and propylene.

In the prior art, purification of the cracking gas obtained usually commences, as shown in FIG. 1, with an oil scrub, followed by a water scrub. Further purification processes are disclosed, for example, in DE 10 2006 045 498 A1 and EP 1 158 038 A2.

FIG. 1 shows the commencement of the purification and fractionation chain for a cracking gas obtained from a liquid hydrocarbon-containing feed, according to the prior art in a schematic view.

The cracking gas 1 is fed into the lower section 21 of a mass transfer column 20 which uses two liquid hydrocarbon fractions 41 and 42 which contain predominantly heavy oils and heavy naphtha as scrubbing medium. The mass transfer column 20 is divided into two sections, an upper section 22 and the abovementioned lower section 21. Separation is effected by means of a chimney neck tray 24 through which the down flowing liquid cannot pass and the descending gas phase can pass.

The mass transfer column 20 has various elements. Cascade trays 23 are located in the lower section of the mass transfer column 21. The upper section 22 likewise contains some cascade trays 23 and also elements having a high effectiveness, for example sieve trays 25. The cracking gas 1 is introduced into the lower section of the mass transfer column 20 and comes into intimate contact with the down flowing scrubbing media 41 and 42. The cracking gas is first and foremost cooled by contact with the scrubbing media 41 and 42. Heavy oil components and solid particles of carbonaceous material are scrubbed out of the cracking gas. The cracking gas 2 which has been freed of the heavy oil components and particles of carbonaceous material leaves the mass transfer column 20 at the top. A liquid phase containing all the solid particles of carbonaceous material and the heavy oil components of the cracking gas is taken off from the bottom of the mass transfer column 20. The mass transfer column 20 is referred to in the prior art as primary oil fractionator, oil scrubbing column or oil scrub.

The cracking gas 2 which has now been freed of heavy oil components and solid particles of carbonaceous material is introduced into the lower part of a scrubbing water column 90. This scrubbing water column 90 is also referred to as water scrub. In the scrubbing water column 90, mainly simple elements such as cascade trays 13 are used in the lower part. In the upper part, there are elements 15 having increased effectiveness, for example sieve trays, valve trays, mesh packing, structured packing and/or beds of random packing elements.

Cold water 31 is introduced as scrubbing medium at the top of the scrubbing water column 90. In the scrubbing water column 90, the ascending cracking gas 2 is freed of further impurities such as petroleum spirit components and cooled further. Accordingly, a liquid fraction 4 which contains mainly the petroleum spirit components and water is taken off from the bottom of the scrubbing water column 90. The gaseous product 5 which leaves the scrubbing water column 90 at the top has now been freed of heavy oil components, petroleum spirit components and solid particles of carbonaceous material and can subsequently be separated into the individual hydrocarbon fractions, in particular ethylene or propylene (not shown in more detail).

It is an object of the present invention to simplify the purification of a cracking gas as is formed in the thermal cracking of liquid hydrocarbon-containing feeds. In particular, the outlay in terms of apparatus should be reduced.

The stated object is achieved by a process and an apparatus having the features of the independent claims. Further advantageous embodiments of the invention are indicated in the dependent claims.

The basic concept of the invention is to purify the cracking gas formed in the thermal cracking of the liquid hydrocarbon-containing feed using only a fraction rich in petroleum spirit and a water-rich fraction in succession as scrubbing media. The complete oil scrubbing column is therefore dispensed with according to the present invention even when using the abovementioned hydrocarbon-containing feeds such as naphtha. The removal of the heavy oil components, the petroleum spirit components and the solid hydrocarbon particles is carried out in a single scrubbing column.

The scrubbing column used in the present invention is similar to scrubbing water columns used in known processes and plants and is, in process engineering terms, divided into a lower section and an upper section. The lower section and the upper section can differ in terms of the elements that are used in these two sections. The cracking gas is conveyed in succession through the lower section and the upper section of the scrubbing column in countercurrent to the liquid scrubbing media, as mentioned a fraction rich in petroleum spirit and a water-rich fraction.

The water-rich fraction is introduced as scrubbing medium into the upper section of the scrubbing column. The fraction rich in petroleum spirit is introduced as scrubbing medium into the lower section of the scrubbing column. The cracking gas comes into intimate contact with the down flowing fraction rich in petroleum spirit in the lower section of the scrubbing column via the elements there. The down flowing fraction rich in petroleum spirit here removes heavy oil components and solid particles of carbonaceous material from the cracking gas. In addition, the ascending cracking gas is cooled. The ascending cracking gas subsequently goes into the upper section of the scrubbing column. Petroleum spirit components (from cracking and from the fraction rich in petroleum spirit used as scrubbing medium in the lower section of the scrubbing column) present in the cracking gas are scrubbed out by means of the water-rich fraction as scrubbing medium in the upper section. Accordingly, a petroleum spirit-water phase is obtained.

For the purposes of the present patent application, a "fraction rich in petroleum spirit" is a fluid which has a high content of petroleum spirit as defined below, i.e. at least 80%, in particular at least 90%, 95% or 99%, of petroleum spirit. It can also be (essentially) pure petroleum spirit. Correspondingly, a "water-rich fraction" is a fraction which has a high water content, i.e. at least 80%, in particular at least 90%, 95% or 99%, of water. A "water-rich fraction" is in particular process water, i.e. essentially pure water which may be additionally treated with appropriate auxiliaries. The "water-rich fraction" can also be separated off from the petroleum spirit-water phase mentioned.

According to the invention, the cracking gas is fed directly into the scrubbing column as first purification step. For the purposes of the invention, a "purification step" or a "purification" is a process step in which one or more prescribed components are removed from the cracking gas. The term "cracking gas" refers to the gas which leaves the cracking furnace. For the purposes of the invention, "mild cracking conditions" are conditions in the cracking furnace under which the thermal cracking of the hydrocarbon-containing feed takes place with mild dissociation severity, i.e. with low cracking severity.

The cracking severity is an important parameter in the process used here for producing olefins by cracking of hydrocarbon-containing feeds. It is determined by the cracking conditions used. The cracking conditions are, in particular, influenced by the temperature and the residence time and also the partial pressures of the components of the hydrocarbon-containing feed and also of the steam. The composition of the hydrocarbon-containing feed and the construction type of the cracking furnace(s) used also influence the cracking conditions. Owing to the interacting influences of these factors, indication of the specific individual parameters is frequently not meaningful. The cracking conditions are therefore also indicated via the ratio of propylene to ethylene in the cracking gas (known as P/E ratio).

Mild cracking conditions lead, for example, to a ratio of propylene to ethylene of at least 0.7 kg/kg, in particular from 0.7 to 1.6 kg/kg, preferably from 0.8 to 1.4 kg/kg, particularly preferably from 0.85 to 1.2 kg/kg, at the outlet of the cracking furnace. Cracking conditions which lead to a ratio of propylene to ethylene at the outlet of the cracking furnace of from 0.75 to 1.5 kg/kg or from 0.8 to 1.2 kg/kg or from 0.85 to 1.15 kg/kg can also be advantageous.

Purely by way of example, the temperature of the cracking gas directly at the outlet of the cracking furnace can be in the range from 720° C. to 800° C. and its pressure can be from 1 barg to 4 barg, preferably from 2.5 barg to 4 barg. The pressures in barg relate to superatmospheric pressure, i.e. 1 barg means 1 bar above atmospheric pressure. The addition of steam to the hydrocarbon-containing feed upstream of the cracking furnace in a mass ratio of steam to hydrocarbons in the hydrocarbon-containing feed in the range from 0.15 kg/kg to 0.45 kg/kg, preferably from 0.2 kg/kg to 0.35 kg/kg, is likewise advantageous.

The invention can, in particular, be useful because relatively large amounts of (pyrolysis) petroleum spirit are formed in the thermal cracking of hydrocarbons of conventional composition, for example naphtha, under mild cracking conditions. This petroleum spirit can be used directly as scrubbing medium, i.e. as the "fraction rich in petroleum spirit", so that the invention does not rely on provision of scrubbing media from outside the plant. The petroleum spirit can also be formed here during start-up of the plant or always when additional petroleum spirit is required. The process of the invention is therefore particularly inexpensive and makes good use of the petroleum spirit which is obtained in any case. Petroleum spirit not used as scrubbing medium can be passed on at the battery limits, fractionated and/or recirculated to the cracking step. The invention therefore always makes it possible to produce precisely the amount of petroleum spirit which is required as scrubbing medium. Losses, for example due to not absolutely complete separation from the petroleum spirit-water phase (see below) and/or due to evaporation, can at any time be compensated from the process itself. A corresponding plant can also be operated under the mild cracking conditions only when petroleum spirit is required as scrubbing medium, for example during start-up.

A corresponding plant can be erected in less space and more cheaply as a result of the use of a single scrubbing column.

For the purposes of the invention, "petroleum spirit", including the abovementioned pyrolysis petroleum spirit, is a hydrocarbon fraction of which 80% boils at a temperature of 130° C. at atmospheric pressure. Such a fraction is completely vaporized at a temperature above 180° C. Accordingly, a petroleum spirit-water phase is a mixture of such a hydrocarbon fraction and water. The terms "petroleum spirit", "petroleum spirit fraction" and "petroleum spirit phase" are used synonymously in the present patent application. It goes without saying that petroleum spirit can also be contaminated to a certain extent with other components, for example other hydrocarbons and water. However, the fraction rich in petroleum spirit which is used as scrubbing medium has at least the abovementioned contents of petroleum spirit or the hydrocarbons which define the boiling point of petroleum spirit.

For the purposes of the invention, "direct" introduction of the cracking gas into the scrubbing column means a direct hydrodynamic connection between cracking furnace and scrubbing column, which connection does not contain an intermediate scrub or a similar purification step. Certain structural measures, for example a pipe with a kink where solid particles or the like can accumulate, are not considered to be an intermediate purification step for the purposes of the invention.

In a preferred embodiment of the invention, the scrubbing column is divided in process engineering terms into the lower section and the upper section by a plate, with no liquid being able to pass from the top downward through the plate. In this embodiment of the invention, the scrubbing column is configured as a two-circuit column. The two parts which have been separated in process engineering terms are each supplied with a separate scrubbing medium, namely the abovementioned petroleum spirit- and water-rich fractions, and have a separate liquid offtake from the bottom of the respective parts. This has the advantage that, where necessary, the scrubbing media of the lower and upper parts can be independent of one another and be altered independently without different columns being necessary.

A liquid phase containing the heavy oil components and particles of carbonaceous material is preferably taken off from the bottom of the scrubbing column, i.e. from the lower section. In this embodiment, the cracking gas leaves the scrubbing column in gaseous form at the top and has been freed of particles of carbonaceous material, heavy oils and a petroleum spirit fraction.

Furthermore, a liquid petroleum spirit-water phase is taken off from the plate which divides the scrubbing column into the lower section and the upper section. This allows this phase to be separated later into a petroleum spirit phase and a water phase, with the two phases being able to be recovered separately as scrubbing media in the form of the petroleum spirit- or water-rich fraction.

In an embodiment of the invention, the liquid phase which is taken off from the plate of the scrubbing column, i.e. from its lower section, is separated into a first liquid phase containing the particles of carbonaceous material and a second liquid phase containing a heavy oil fraction. This allows the separate further processing or separate recovery of the individual constituents of the liquid phase from the bottom of the scrubbing column. Any light hydrocarbons (preferably hydrocarbons having 4 and 5 carbon atoms) present in the second liquid phase are advantageously stripped from this phase and recirculated to the scrubbing column. The liquid petroleum spirit-water phase is, as mentioned, advantageously separated into a liquid petroleum spirit fraction and a liquid water fraction, with the liquid petroleum spirit fraction being at least partly introduced as scrubbing medium into the lower part of the scrubbing column as the fraction which is rich in petroleum spirit and the liquid water fraction being at least partly introduced into the upper part of the scrubbing column as the water-rich fraction as scrubbing medium. This allows recycling of the individual phases.

For the purposes of the invention, a heavy oil fraction is a hydrocarbon fraction of which 80% boils at a temperature of 460° C. at atmospheric pressure. At a temperature above 560° C., such a fraction is vaporized completely. Correspondingly, an oil-water phase is a mixture of such a heavy oil fraction and water.

Simple elements, particularly preferably cascade trays, are preferably used in the lower section of the scrubbing column and elements having higher effectiveness, particularly preferably sieve trays, valve trays, mesh packing, structured packing and/or beds of random packing elements, are preferably used in the upper section of the scrubbing column.

The present invention makes it possible, in particular, to reduce the apparatus in the purification of a cracking gas as is formed in the cracking of a liquid hydrocarbon-containing feed. The present invention enables an entire scrubbing column, viz. the primary oil fractionator, to be omitted even in the case of "heavy" feeds such as naphtha. According to the present invention, the cracking gas is freed of heavy oil, petroleum spirit components and solid particles of carbonaceous material in one scrubbing column in which a water-rich fraction is introduced as scrubbing medium at the top of an upper section and further a fraction rich in petroleum spirit, which can be produced by the process itself, is introduced into a lower section.

The invention is illustrated below with the aid of two examples depicted in the figures.

Figure 1:
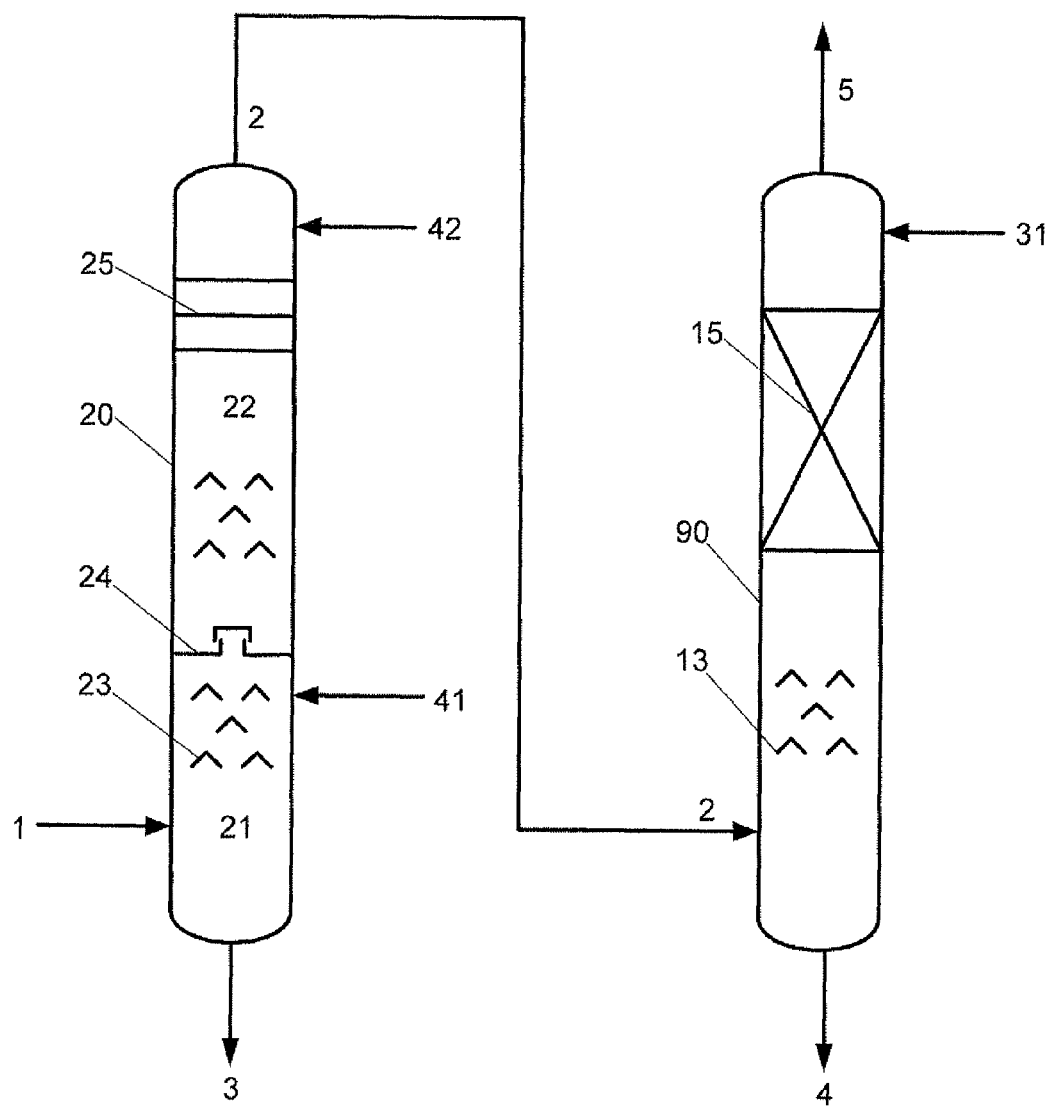
FIG. 1 shows the commencement of the purification sequence according to the prior art.
Figure 2:
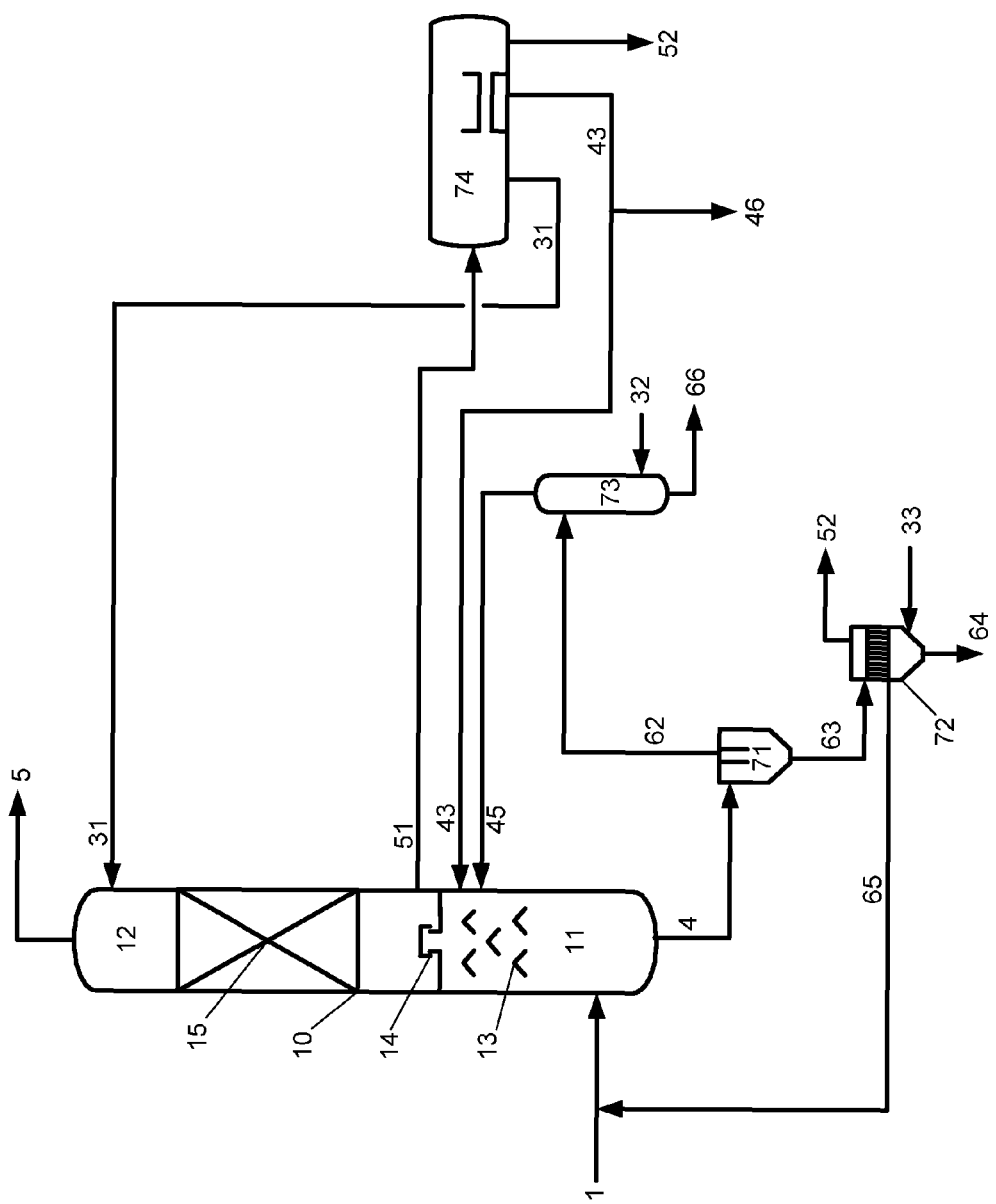
FIG. 2 shows an embodiment of the invention using simple gravity separators and FIG. 3 shows an alternative embodiment of the invention using a multistage gravity separator.

In the examples shown in FIG. 2, the cracking gas 1 is fed directly from the cracking furnace into the lower section 11 of the scrubbing column 10. The scrubbing column 10 is divided in process engineering terms into the lower section 11 and an upper section 12 by means of a chimney neck tray 14. The lower section 11 contains mainly simple elements such as cascade trays. Cascade trays are, in this embodiment, angle elements which are arranged in the lower part in such a way that the peak of the angle points upward.

Elements 15 of higher effectiveness are located in the upper part 12 of the scrubbing column 10. These can be, for example, structured packing and/or beds of random packing elements.

Water or a water-rich fraction 31 is introduced as scrubbing medium into the upper section 12 of the scrubbing column 10. A liquid fraction 43 rich in petroleum spirit is introduced as scrubbing medium into the lower section 11 of the scrubbing column 10. The cracking gas 1 is fed into the lower part 11 of the scrubbing column 10 and comes into intimate contact with the down flowing scrubbing medium 43 via the elements 13. The down flowing liquid fraction 43 rich in petroleum spirit here removes oils and solid particles of carbonaceous material from the cracking gas 1. In addition, the ascending cracking gas 1 is cooled. The ascending cracking gas 1 passes through the chimney neck tray 14 and goes into the upper part 12 of the scrubbing column 10.

The chimney neck tray 14 is configured so that the down flowing water-rich fraction 31 from the upper section 12 of the scrubbing column 10 cannot pass through it. The gas phase passing through the chimney neck tray 14 has already been freed of all solid particles of carbonaceous material and of heavy oils but still contains heavy petroleum spirit impurities. These petroleum spirit impurities are scrubbed out in the upper part using the water-rich fraction 31 as scrubbing medium. A mixed petroleum spirit-water phase 51 accordingly collects on the chimney neck tray 14 and is taken off from the chimney tray 14.

The petroleum spirit-water phase 51 which has been taken off is fed to a petroleum spirit-water separator 74. There, an aqueous phase separates out and is recirculated as water-rich fraction 31 to the top of the scrubbing column 10. The petroleum spirit phase which has separated out in the petroleum spirit-water separator 74 is fed as fraction 43 which is rich in petroleum spirit to the lower part of the scrubbing column 10. In addition, a further water phase 52 is obtained in the petroleum spirit-water separator 74 and is integrated into the process water circuit of the plant. In addition, part of the petroleum spirit phase (the excess which is not required for the petroleum spirit circuit of the water scrub) is separated off as petroleum spirit product 46 and is exported to further processing (for example petroleum spirit hydrogenation or isolation of aromatics) and/or cracked again.

A liquid phase 4 containing all heavy oil components and particles of carbonaceous material is taken from the bottom of the scrubbing column 10. The liquid phase 4 taken off is firstly fed into a centrifugal separator (cyclone) 71. The solid particles of carbonaceous material preferably settle out at the bottom in the centrifugal separator 71 and are fed in a liquid fraction 63 into a filter system 72. A liquid fraction 62 which now contains only very fine solid particles of carbonaceous material is taken off at the top of the centrifugal separator 71. This is fed to a stripper 73 where a gaseous hydrocarbon fraction 45 (mainly hydrocarbons having from 4 to 9 carbon atoms) is stripped out by introduction of steam 32 and is reintroduced into the lower section 11 of the scrubbing column 10. A heavy oil phase 66 is taken off from the bottom of the stripper 73. In the filter system 72, the solid particles of carbonaceous material are separated from the liquid phase 65 which is recirculated to the cracking gas stream 1. To remove the particles 64 of carbonaceous material from the filter system 72, the latter is supplied with steam 33. As a result, the stream 64, which contains all the solid particles of carbonaceous material, is free of volatile hydrocarbons and can thus be taken from the filter system 72 and disposed of. In addition, an offgas 52 is formed.

Figure 3:
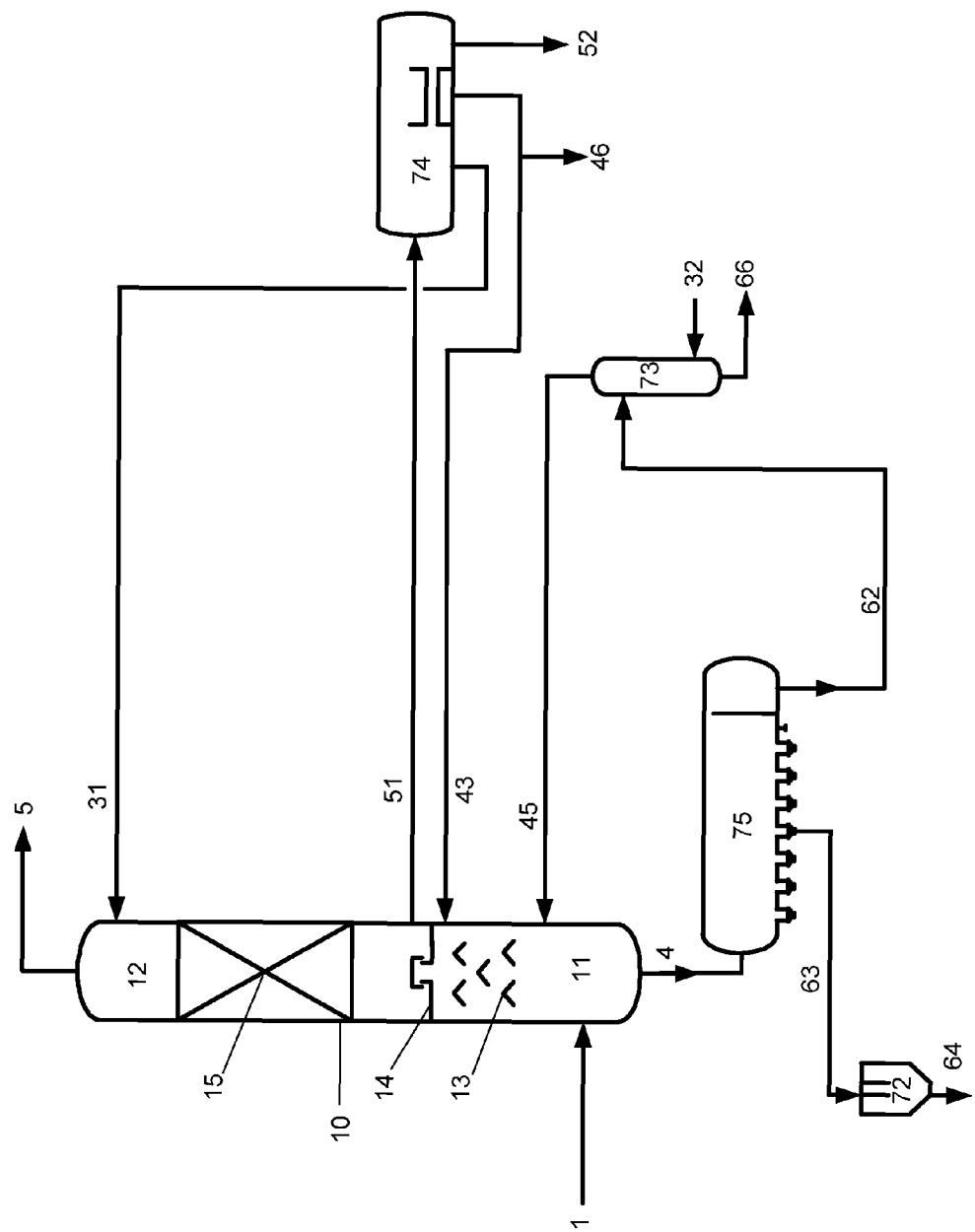

In this embodiment of the invention as shown in FIG. 2, the cracking gas 1 leaves the scrubbing column 10 via the top 5 and, as overhead product 5, has been freed of heavy oil components, petroleum spirit components and solid particles of carbonaceous material. The cracking gas 5 which has been purified in this way can then be passed to the further low-temperature fractionation in which, in particular, the desired products ethylene and propylene can be separated off from the cracking gas 5. The example shown in FIG. 3 resembles the example shown in FIG. 2. Identical parts and streams have here been denoted by the same reference numerals.

Here too, the scrubbing column 10 consists of a lower section 11 and an upper section 12, with the two sections being separated in process engineering terms by a chimney neck tray 14. In a manner analogous to the example shown in FIG. 2, water 31 is introduced as scrubbing medium at the top of the upper section 12. In a manner analogous to the example of FIG. 2, a petroleum spirit-water phase 51 is taken off from the bottom of the upper section 12 and is, in a manner similar to the example shown in FIG. 2, separated into the individual constituents. This is not shown further here.

In contrast to the example shown in FIG. 2, a liquid phase 4 is taken off from the bottom of the lower section 11 and fed directly into a multiple gravity separator 75. The multiple gravity separator 75 has a plurality of depressions in which the solid particles of carbonaceous material collect. A liquid phase 63 which contains all the particles of carbonaceous material is taken off from these depressions. The liquid phase 63 is fed into a filter system 72 and treated analogously to the example indicated in FIG. 2 (not shown).

A hydrocarbon fraction 62 which now contains only very fine particles of carbonaceous material is likewise obtained in the multiple gravity separator 75 and is treated in a manner analogous to the example of FIG. 2. The treatment of the water fraction 31 and the petroleum spirit-water phase 51 likewise corresponds to that indicated in the example of FIG. 2. Identical streams and apparatuses have been provided with the same reference numerals in both examples.

The invention claimed is:

1. A process for producing olefins, comprising:
    feeding a hydrocarbon-containing feed into a cracking furnace where hydrocarbons of the hydrocarbon-containing feed are at least partly cracked to form a cracking gas encompassing ethylene and propylene, and
    passing said cracking gas (1) in succession through a lower section (11) and an upper section (12) of a scrubbing column (10), wherein a fraction (43) rich in petroleum spirit is used in said lower section (11) of the scrubbing column (10) as liquid scrubbing medium in countercurrent flow to said cracking gas, and a water-rich fraction (31) is used in said upper section (12) of the scrubbing column (10) as liquid scrubbing medium in countercurrent flow to said cracking gas, wherein said fraction (43) rich in petroleum spirit is a hydrocarbon fraction of which 80% boils at a temperature of 130° C. at atmospheric pressure,
    wherein said scrubbing column (10) is divided into said lower section (11) and said upper section (12) by a tray (14),
    wherein a liquid petroleum spirit-water phase (51) is taken off from said tray (14) of said scrubbing column (10), and said liquid petroleum spirit-water phase (51) is separated into a liquid petroleum spirit fraction and a liquid water fraction and,
    wherein said liquid petroleum spirit fraction is at least partly introduced into the lower section (11) of said scrubbing column (10) as said fraction (43) rich in petroleum spirit, and said liquid water fraction is at least partly introduced as said water-rich fraction (31) into the upper section (12) of said scrubbing column (10).

2. The process as claimed in claim 1, wherein said cracking furnace is operated under conditions such that the cracking gas (1) contains propylene and ethylene in a propylene to ethylene ratio of at least 0.7 kg/kg.

3. The process as claimed claim 1, wherein said cracking gas (1), directly at the output of the cracking furnace, has a temperature in the range from 720° C. to 800° C. and/or a pressure in the range from 1 barg to 4 barg.

4. The process as claimed in claim 1, wherein a liquid phase (4) containing heavy oils and particles of carbonaceous material is taken off from the bottom of said scrubbing column (10) and a cracking gas (5) freed of particles of carbonaceous material, heavy oils, and a petroleum spirit fraction is discharged from the top of said scrubbing column (10).

5. The process as claimed in claim 4, wherein said liquid phase (4) taken off from the bottom of the scrubbing column (10) is separated into a first liquid phase (63) containing the particles of carbonaceous material and a second liquid phase (62) containing a heavy oil fraction.

6. The process as claimed in claim 5, wherein light hydrocarbons (45) present in the second liquid phase (62) are stripped out of said second liquid phase (62) and are recirculated to the scrubbing column (10).

7. The process as claimed in claim 1, wherein said lower section (11) of the scrubbing column (10) contains cascade trays and said upper section (12) of the scrubbing column (10) contains sieve trays, valve trays, mesh packing, structured packing and/or beds of random packing elements.

8. The process as claimed in claim 1, wherein part of said fraction (43) rich in petroleum spirit used as the scrubbing medium in the lower section (11) of the scrubbing column (10) is obtained from the hydrocarbon-containing feed.

9. The process as claimed claim 1, wherein said cracking gas (1), directly at the output of the cracking furnace, has a temperature in the range from 720° C. to 800° C. and/or a pressure in the range from 2.5 barg to 4 barg.

10. The process as claimed in claim 1, wherein said tray (14) is a chimney neck tray.

11. The process as claimed in claim 1, wherein said cracking furnace is operated under conditions such that the cracking gas (1) contains propylene and ethylene in a propylene to ethylene ratio of from 0.7 kg/kg to 1.6 kg/kg.

12. The process as claimed in claim 1, wherein steam is added to the hydrocarbon-containing feed upstream of the cracking furnace so that the mass ratio of steam to hydrocarbons in the hydrocarbon-containing feed is in the range from 0.15 kg/kg to 0.45 kg/kg.

13. The process as claimed in claim 5, wherein said liquid phase (4) taken off from the bottom of the scrubbing column (10) is separated in a centrifugal separator into said first liquid phase (63) containing the particles of carbonaceous material and said second liquid phase (62) containing the heavy oil fraction.

14. The process as claimed in claim 13, wherein said first liquid phase (63) containing the particles of carbonaceous material is sent to a filter (72) wherein a stream containing the particles of carbonaceous material (64) is separated from a liquid phase (65) and wherein the liquid phase (65) is recirculated to the cracking gas (1).

15. The process as claimed in claim 5, wherein light hydrocarbons (45) present in the second liquid phase (62) are stripped out of said second liquid phase (62) and are recirculated to the lower section (11) of said scrubbing column (10).

* * * * *